(12) United States Patent
Fischell et al.

(10) Patent No.: US 7,651,520 B2
(45) Date of Patent: *Jan. 26, 2010

(54) MEANS AND METHOD FOR THE ACCURATE PLACEMENT OF A STENT AT THE OSTIUM OF AN ARTERY

(75) Inventors: Robert E. Fischell, Dayton, MD (US); Tim A. Fischell, Kalamazoo, MI (US); David R. Fischell, Fair Haven, NJ (US); Mark E. Zyzelewski, Kalamazoo, MI (US)

(73) Assignee: Ostial Solutions, LLC, Kalamazoo, MI (US)

(*) Notice: Subject to any disclaimer, the term of this patent is extended or adjusted under 35 U.S.C. 154(b) by 88 days.

This patent is subject to a terminal disclaimer.

(21) Appl. No.: 11/975,196

(22) Filed: Oct. 18, 2007

(65) Prior Publication Data

US 2008/0082155 A1 Apr. 3, 2008

Related U.S. Application Data

(63) Continuation-in-part of application No. 11/442,719, filed on May 30, 2006, now abandoned.

(51) Int. Cl.
*A61F 2/06* (2006.01)
*A61M 25/01* (2006.01)

(52) U.S. Cl. ..................... 623/1.11; 606/108

(58) Field of Classification Search ............... 623/1.11, 623/1.12, 1.13, 1.15, 1.35; 606/108, 191–200; 604/104–109, 103.04, 164.1–167.01, 192
See application file for complete search history.

(56) References Cited

U.S. PATENT DOCUMENTS

| | | | | | |
|---|---|---|---|---|---|
| 4,738,666 | A | * | 4/1988 | Fuqua | 604/514 |
| 5,147,302 | A | * | 9/1992 | Euteneuer et al. | 604/103 |
| 5,464,408 | A | * | 11/1995 | Duc | 606/108 |
| 5,653,684 | A | * | 8/1997 | Laptewicz et al. | 604/22 |
| 5,749,890 | A | | 5/1998 | Shaknovich | |
| 5,800,457 | A | * | 9/1998 | Gelbfish | 606/200 |
| 6,059,814 | A | * | 5/2000 | Ladd | 606/200 |
| 6,152,944 | A | * | 11/2000 | Holman et al. | 623/1.11 |
| 6,293,964 | B1 | * | 9/2001 | Yadav | 623/1.11 |
| 6,344,045 | B1 | * | 2/2002 | Lim et al. | 606/108 |
| 6,355,051 | B1 | * | 3/2002 | Sisskind et al. | 606/200 |
| 6,458,151 | B1 | | 10/2002 | Saltiel | |
| 6,676,693 | B1 | * | 1/2004 | Belding et al. | 623/1.11 |
| 7,105,013 | B2 | * | 9/2006 | Durcan | 623/1.11 |
| 2004/0181272 | A1 | * | 9/2004 | Chambers | 623/1.11 |

* cited by examiner

*Primary Examiner*—Anhtuan T Nguyen
*Assistant Examiner*—Elizabeth Houston

(57) ABSTRACT

Disclosed is an ostial stent positioner that has the form of a wire for most of its length and having a short cylinder with a longitudinal slit and expandable legs situated at the positioner's distal end. The slit cylinder with its attached wire acts as an introducer sheath to introduce a stent delivery system with a stent into the artery that is to be stented. A second aspect of the present invention is a method for accurately placing a stent at the ostium of an artery that would have an ostial stenosis. Examples of such arteries that have ostial stenoses are the right and left main coronary arteries, a saphenous vein graft as used in coronary bypass surgery and the renal arteries. Also disclosed are designs for the slit cylinder that provides a variable diameter so as to fit snugly within guiding catheters having different inside diameters.

18 Claims, 4 Drawing Sheets

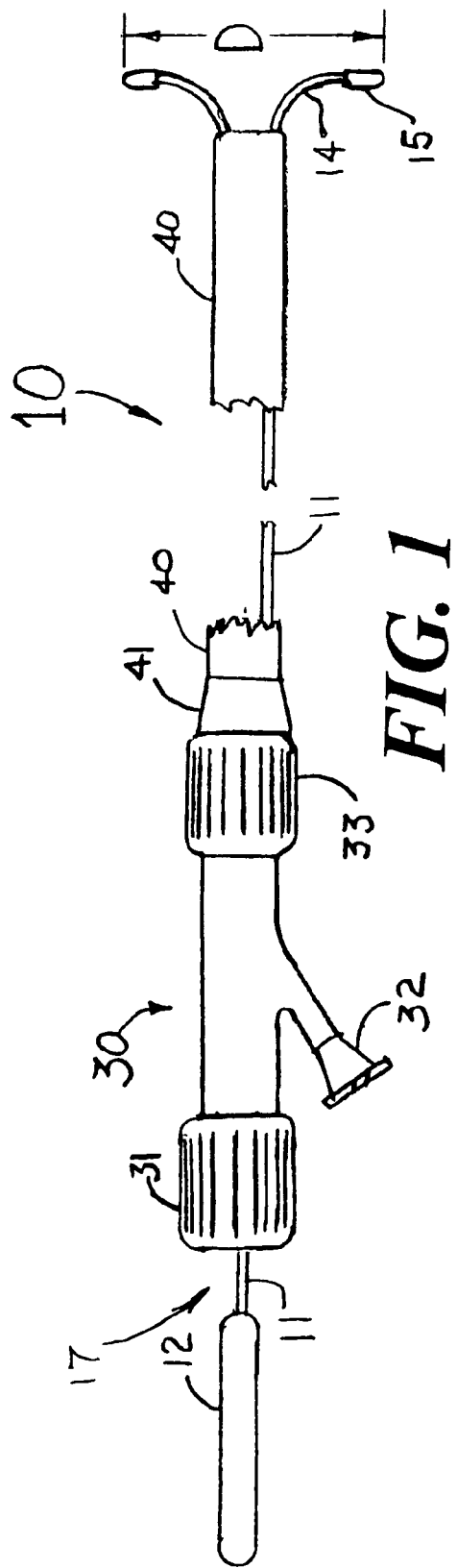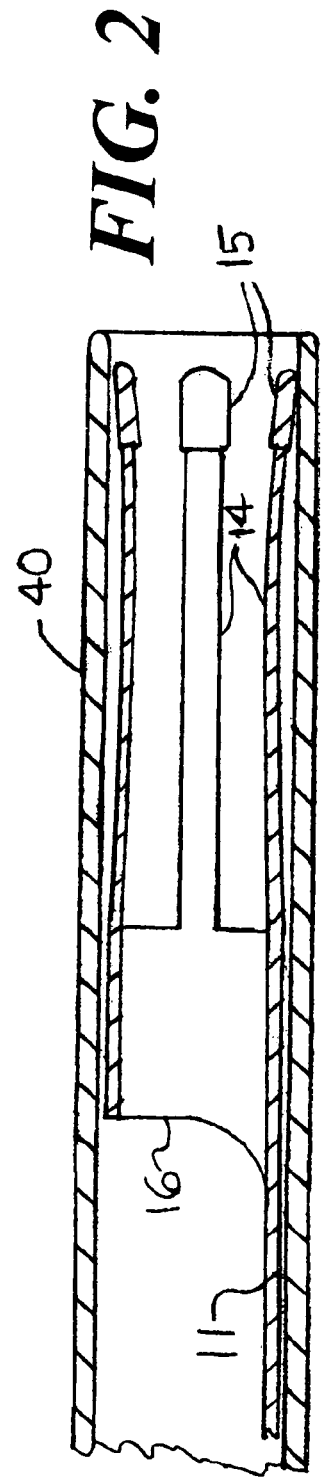

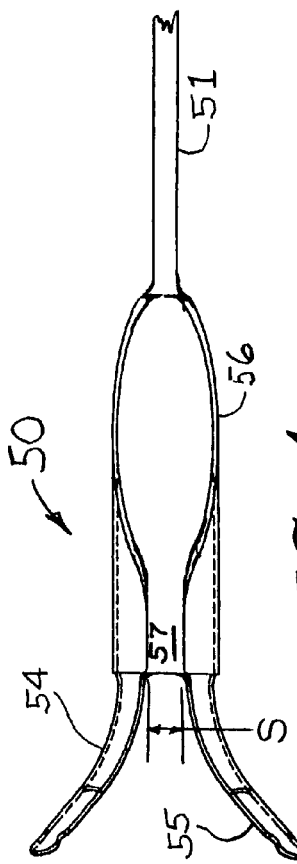
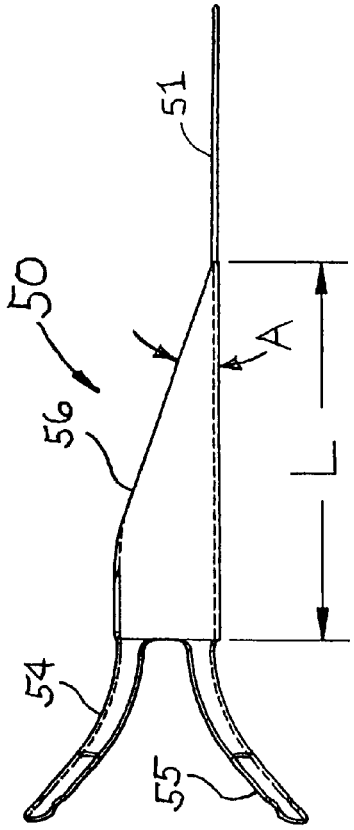
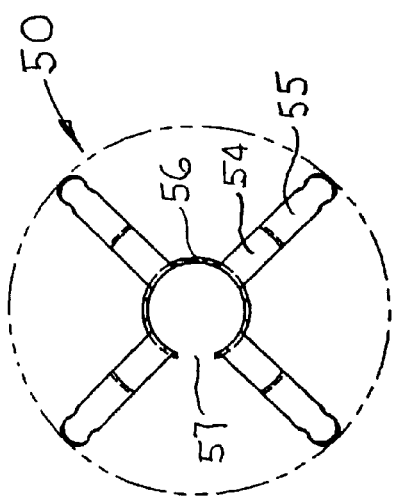
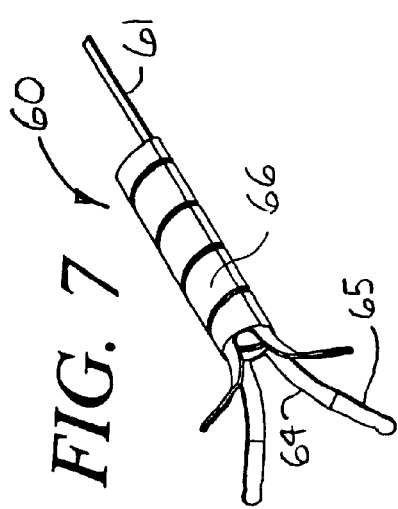

MEANS AND METHOD FOR THE ACCURATE PLACEMENT OF A STENT AT THE OSTIUM OF AN ARTERY

REFERENCE TO A PREVIOUS PATENT APPLICATION

This is a continuation-in-part application of the patent application Ser. No. 11/442,719 filed on May 30, 2006 now abandoned.

FIELD OF USE

This invention is in the field of devices for placing stents within a stenosis that extends to or near the ostium of an artery.

BACKGROUND OF THE INVENTION

Although most stenoses do not occur at the ostium of an artery, there are thousands of cases each month where the mouth of an artery (the ostium) is substantially obstructed at its aortic take-off; this is called an aorto-ostial lesion. In such cases, the interventional cardiologist or radiologist is frequently unable to place the stent's proximal end within ±2 mm of the ostial plane. Two types of incorrect stent positions are (1) when the stent's proximal end extends more than 2 mm into the aorta, and (2) when the stent's proximal end is placed more than 1-2 mm into the artery distal to the ostial plane.

In U.S. Pat. No. 6,458,151, F. S. Saltiel describes an ostial stent positioning device. However, the most important feature of such a device; namely, and expandable distal portion that touches the wall of the aorta near the ostium of the artery to be stented is not optimized for easy usage of such a device. Furthermore, the Saltiel design is essentially a cylindrical sheath within the guiding catheter which sheath extends for the entire length of the guiding catheter. Such a design would have an incredible amount of friction between the cylindrical sheath and the interior wall of the guiding catheter that would make it very difficult to operate. In addition, the Saltiel design would substantially obstruct the internal cross-section of the guiding catheter along its entire length, limiting the injection of contrast material, and the passage of guide wires, balloon catheters, and/or stents.

In U.S. Pat. No. 5,749,890, A. Shaknovich utilizes a stent mounted on a catheter that has an inflatable section that touches the wall of the aorta in the vicinity of the ostium of the artery that is to be stented. Such a design precludes an accurate stent positioning system that can be used with the stent delivery system of any manufacturer.

SUMMARY OF THE INVENTION

A first aspect of the present invention is an ostial stent positioner that has the form of a wire for most of its length and having a short cylinder with expandable legs situated at the positioner's distal end. The cylinder with its attached wire acts as an introducer sheath to introduce a stent delivery system with a stent into the artery that is to be stented. A second aspect of the present invention is a method for accurately placing a stent at the ostium of an artery that would have an ostial stenosis. Examples of such arteries that have ostial stenoses are the right and left main coronary arteries, a saphenous vein graft as used in coronary bypass surgery and the renal arteries. Each of these arteries has an ostium situated at the aorta.

The preferred method for using this invention would be to first back-load the ostial stent positioner within a guiding catheter. A guide wire could then be loaded through the guiding catheter, and through the pre-deployed ostial positioning system that had already been placed within the guiding catheter. The guiding catheter would be advanced over the guide wire into the aorta. The next action would be to place the guiding catheter through the aorta in a conventional manner so that its distal end will be engaged within or near the ostium of the artery that is to be stented. The guide wire would then be advanced through the guiding catheter until its distal end was placed distal to the stenosis. If pre-dilitation of the ostial stenosis was needed, a balloon angioplasty catheter would be advanced over the guide wire and through the guiding catheter and the catheter's balloon would be inflated to pre-dilate the stenosis. After the balloon angioplasty catheter was removed from the guiding catheter (or if no pre-dilatation was required) then a stent delivery system with the appropriately sized stent would be advanced over the guide wire until the stent's proximal end lay at or distal to the ostium of the artery. The stent delivery system would typically have its proximal radiopaque marker band placed distal to the ostial plane of the artery to be stented. While retaining the guide wire and a distal portion of the stent delivery system in the artery, the guiding catheter with the positioner inside would then be pulled back a short distance into the aorta. The positioner would then be advanced until its expandable legs at the positioner's distal end extended beyond the guiding catheter's distal end, thus allowing the expandable legs to expand. The guiding catheter would then be advanced until its distal end surface pushes gently against the positioner's expandable legs to engage the legs against the wall of the aorta and generally align the legs at the ostium of the artery that is to be stented. The plane of the "feet" which are located at the distal ends of the expandable legs, would then be situated at the artery's ostial plane. The outer diameter of the feet would be larger than the diameter of the artery to be stented. Since the expandable legs would have feet that would be formed from a material that included a radiopaque substance or from a metal that is coated with or made from a radiopaque metal, the interventional cardiologist who is performing this procedure would have a clear angiographic/fluoroscopic marker of the ostial plane of the artery that is to have a stent placed within the ostial stenosis of that artery. The interventional cardiologist would then pull the stent delivery system back until the proximal radiopaque marker band within the balloon of the stent delivery system was aligned appropriately relative to the radiopaque feet of the expandable legs. The balloon would then be inflated to deliver the stent accurately at the ostial stenosis with the stent's proximal end lying within 2 mm of the ostial plane of the artery (typically just proximal to the true ostial plane). It is expected that an experienced interventional cardiologist could place the proximal end of the stent within 1.0 mm and just proximal to the ostial plane.

In a prior application one embodiment of this invention was described that requires a separate introducer device that is used to place the positioner into the guiding catheter. This continuation-in-part application teaches an improved embodiment of the invention that allows the sheath-like ostial stent positioner to be placed into the guiding catheter without requiring a separate introducer device.

The main object of this invention is to describe a means and method for accurately placing the proximal end of a stent within ±2 mm of the ostial plane of an artery that has a stenosis located at or near the ostium of that artery.

Another object of this invention is to place the proximal end of a stent within ±2.0 mm of the ostial plane of an artery that has a stenosis located at or near the artery's ostium.

Still another object of the present invention is to teach a method for accurately placing a stent within an ostial stenosis.

Still another object of the present invention is to utilize a variable diameter slit cylinder to which the expandable legs are connected, which variable diameter cylinder is designed to expand radially outward so as to create gentle contact between the cylinder's outer surface and the interior surface of the guiding catheter.

Still another object of this invention is to have the expandable legs go out to an angle as great as 90 degrees relative to the axis of the positioner so as to fit most smoothly against the wall of the aorta.

Still another object of this invention is to have the wire that joins to the slit cylinder have a colored handle at its most proximal section and have a decreased wire thickness for the length of the wire that is closest to the slit cylinder so as to have increased flexibility at that portion that lies in the curved section of the guiding catheter.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 1 is a side view of a Touhy-Borst fitting, a guiding catheter and an ostial stent positioner that acts as an introducer sheath for placing the proximal end of a stent in close proximity to the ostial plane of an artery that has an ostial stenosis.

FIG. 2 is a longitudinal cross section of a distal portion of the ostial stent positioner located within the guiding catheter showing the expandable legs in their folded state.

FIG. 4 is a top view of an alternate embodiment of the present invention using a slit cylinder with expandable legs.

FIG. 5 is an end view of the embodiment of FIG. 4.

FIG. 6 is the side view of the embodiment of FIG. 4.

FIG. 7 is a perspective view of an alternative embodiment of the invention using a helical coil cylinder for improved flexibility.

DETAILED DESCRIPTION OF THE INVENTION

Figure 3:
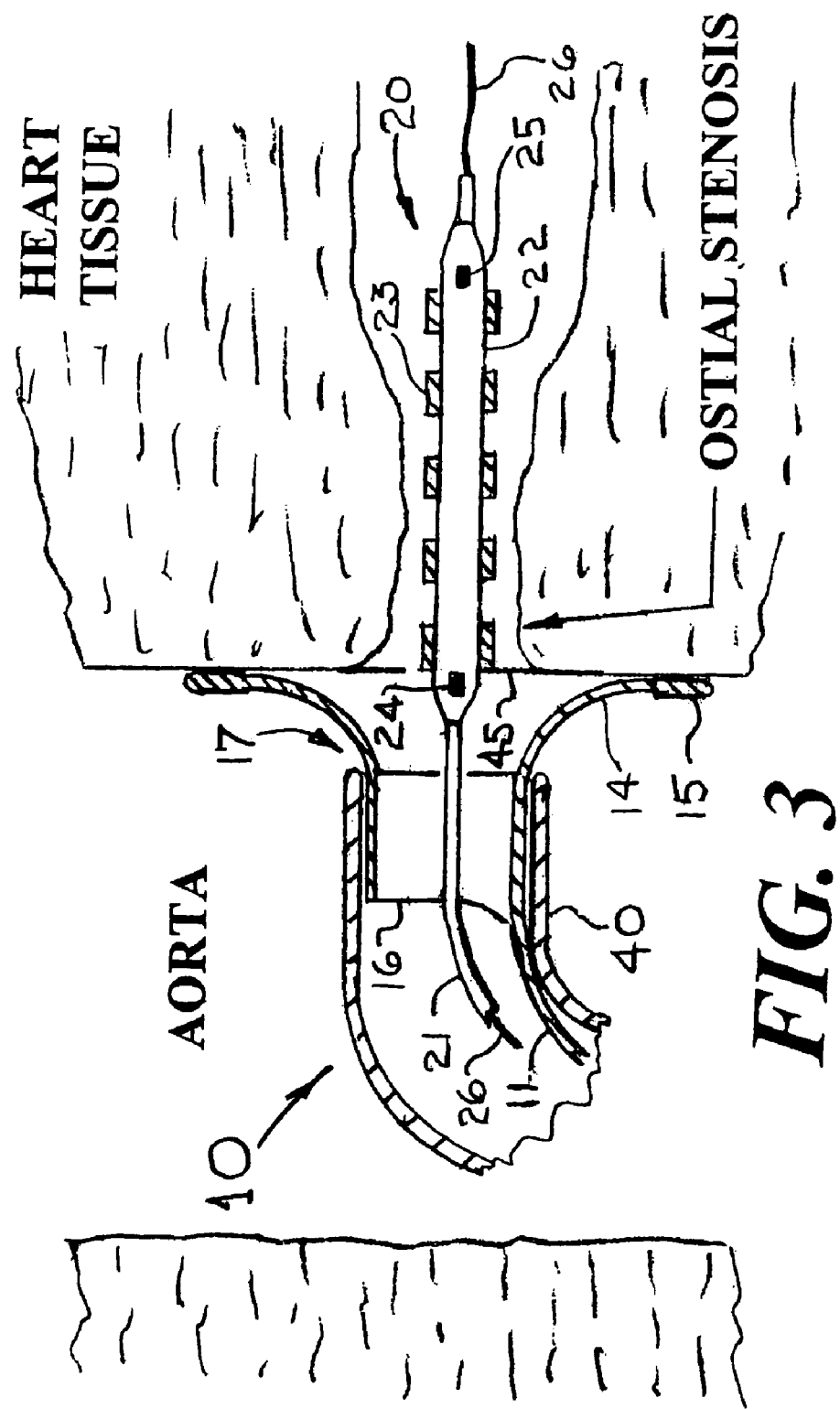
FIG. 3 is a cross section of the distal portions of the guiding catheter, a stent on a stent delivery system and the positioner showing the distal end plane of the feet of the expandable legs placed at the ostial plane of an artery having an ostial stenosis.

FIG. 1 is a side view of a catheter system 10 whose object is to accurately place a stent with its proximal end being situated close to the ostial plane of an artery having an ostial stenosis. The catheter system 10 includes the guiding catheter 40 and an ostial stent positioner 17 that has a wire 11 which connects a small diameter handle 12 to a cylinder 16 (shown in FIG. 2) which has expandable distal end legs 14 with radiopaque feet 15. The guiding catheter 40 that has a proximal Luer fitting 41 that is joined to a Touhy-Borst fitting 30. When the feet 15 are fully expanded, the diameter "D" would typically be between 4 and 10 mm for coronary artery stenting and between 5 and 15 mm for stenting a renal artery. When the expandable legs 14 with radiopaque feet 15 are fully expanded they would have the general appearance of the petals of a flower. When the legs 15 are pushed forward beyond the distal end of the guiding catheter 40, they expand radially outward as shown in FIGS. 1 and 3 from the force of the end of the guiding catheter pushing on the legs 14. When the handle 12 is pulled back, the legs 15 are retracted into the guiding catheter 40 and then the positioner 17 can be pulled out of the guiding catheter 40 after the stent has been placed into the ostial stenosis.

The Touhy-Borst fitting 30 has an adjustable seal fitting 31 (which is a hemostasis valve) that can initially be slightly loosened to allow the positioner 17 to be advanced or pulled back through the guiding catheter 40 without excessive blood leakage. When the expandable legs 14 are in their correct position for placement at the ostial plane of a stenosed artery, (as seen in FIG. 3) the adjustable seal fitting 31 can be tightened to hold a fixed position of the legs 23 relative to the guiding catheter 40 during stent deployment. The Luer fitting 32, being in fluid communication with the lumen of the guiding catheter 40, can be used for flushing the lumen with saline solution and/or for injecting contrast medium. The Luer connector 33 is used to form a removable fluidic seal with the Luer fitting 41 of the guiding catheter 40.

FIG. 2 is an enlarged cross section of the distal portions of the guiding catheter 40 and the positioner 17. The positioner 17 is shown with its expandable legs 14 in their unexpanded state within the guiding catheter 40. In this state, the guiding catheter 40 can be advanced through an introducer sheath at the patient's groin until its distal end is within the ostium of the artery that is to be stented. Furthermore, in this state, both a guide wire and a stent delivery system can be advanced through the guiding catheter 40 and positioner 17 and through the ostial stenosis. The fixed diameter cylinder 16 is attached at its proximal end to the wire 11 and at its distal end to each of the four legs 14. Although 3 legs 14 (of an actual 4 legs) are shown in FIG. 2, as few as 2 or as many as 16 of petal-like legs 14 could be used for an effective array of expandable legs 14.

FIG. 3 is a cross section of a distal portion of the catheter system 10 shown with the distal plane 45 of the radiopaque feet 15 placed at the ostial plane of a stenosed artery. The feet 15 are attached to the expandable legs 14 that are attached to the cylinder 16 which has its position within the guiding catheter 40 adjusted by means of the wire 11. Any such placement of the feet 15 can be defined as having their distal plane 45 "co-planar" with the ostial plane of the artery that has an ostial stenosis. FIG. 3 also shows a guide wire 26 placed through the stent delivery system 20 which has a shaft 21, a proximal radiopaque marker band 24, a distal radiopaque marker band 25 and a stent 23 mounted onto a balloon 22. The ostial stent positioner 17 would be designed to introduce essentially any commercially available stent delivery system 20 into an arterial stenosis. Thus, any interventional cardiologist could use the positioner 17 with any stent delivery system that he or she favors. FIG. 3 also shows how the guiding catheter 40 can be used to gently push the feet 15 against the wall of the aorta at the ostium of the stenosed artery. It is also possible to push the feet 15 against the wall of the aorta by pushing the positioner 17 in a distal direction without the assistance of the guiding catheter 40.

At the start of the stenting procedure, a distal portion of the ostial stent positioner 17 would be positioned as shown in FIG. 2 with the expandable legs 14 placed inside the guiding catheter 40. The catheter system 10 and the guide wire 26 could then be advanced through a conventional introducer sheath (not shown) typically placed at the groin of the patient into whom the stent 23 is to be placed. A 0.014 inch diameter guide wire 26 would be placed into and through the ostial stenosis and the guiding catheter 40 would be advanced until its distal tip was placed through the arterial ostium. The stent delivery system 20 would then be advanced over the guide wire 26 and through the guiding catheter 40 and positioner 17 until the proximal radiopaque marker band 24 was positioned just distal to the ostium of the stenosed artery. The guiding catheter 40 would then be pulled back into the aorta. The positioner 17 (which was already back loaded into the guiding catheter 40) would then be advanced through the guiding catheter 40 until the expandable legs 14 extended out of the distal end of the guiding catheter 40. The guiding catheter 40 would then be pushed gently forward in a distal direction so as to obtain the configuration as generally shown in FIG. 3.

With the configuration as shown in FIG. 3, the interventional cardiologist would be able to clearly visualize the distal plane 45 of the radiopaque feet 15 and also visualize the proximal radiopaque marker band 24. When the radiopaque marker band 24 is pulled backward until it is co-planar with feet 15, then the proximal end of the stent 23 would be placed within ±2 mm of the plane of the ostium of the vessel which is to be stented. The balloon 22 would then be inflated to deliver the stent 23 into the ostial stenosis. Thus, an interventional cardiologist should be able to readily place the proximal end of the stent 23 within ±2 mm of the ostial plane. With some experience, it is expected that the proximal end of the stent 23 could be placed within at least ±1.0 mm of the ostial plane and probably within ±0.5 mm. The optimum placement of the proximal end of the stent 23 is that it extends approximately 0.5 mm into the lumen of the aorta.

Although one method for accurately placing the stent 23 into an ostial stenosis has been described herein, it should be understood that there are several other ways that the present invention could be used to provide accurate stent positioning within an ostial stenosis. For example, the guiding catheter 40 with the positioner 17 in place as shown in FIG. 2 could first be placed over a 0.035 inch diameter guide wire and into the lumen of the ostial stenosis. That larger diameter guide wire could then be removed and the 0.014 inch diameter guide wire 26 could be placed through the stenosis. The stent delivery system 20 could then be advanced over that guide wire 26 and positioned as shown in FIG. 3. The guiding catheter could then be pulled back and the expandable legs 14 could then be deployed as described herein. An important feature of the system 10 is that the guiding catheter 40 and positioner 17 could be held to be motionless while the guide wire 26 or the stent delivery system 20 could be advanced forward or pulled back to obtain an accurate positioning of the stent 23 within the ostial stenosis.

FIGS. 4, 5 and 6 illustrate an alternative embodiment ostial stent positioner 50 utilizing a slit cylinder 56 that would replace the fixed diameter cylinder 16 of FIGS. 2 and 3. The slit cylinder 56 is designed to join to a wire 51 that is equivalent to the wire 11 of FIGS. 1, 2 and 3, which wire 51 is used to move the ostial stent positioner 50 within the guiding catheter 40. The wire 11 of FIGS. 1, 2 and 3 was a conventional small diameter, round wire. The wire 51 of FIGS. 4 and 6 is a flat wire. It should be understood that the term "wire" should include any structure whose cross section is round or a small diameter cylinder or a flat wire or a wire whose cross section is an arc of a circle that is less than 270 degrees. The attachment of the wire 51 to the slit cylinder 56 can be by means of welding, soldering or (with a somewhat different configuration) by means of a biocompatible adhesive. It is also conceived that the slit cylinder 56 and the wire 51 can be formed from a single piece of metal. The slit 57 of the slit cylinder 56 provides a spring-like action to allow the slit cylinder 56 to have a slight outward force against the inner wall of the guiding catheter 40. The outside diameter of the slit cylinder 56 when free in air would have a diameter that is slightly larger than the inside diameter of the largest diameter guiding catheter 40 that would be use for a particular procedure. But the slit 57 would allow the outside diameter of the slit cylinder 56 to compress to fit into any size guiding catheter that would typically be used for ostial stenting. The slit 57 would have a width "S" (as seen in FIG. 4) that is typically between 0.2 and 1.5 mm. The length "L" of the slit cylinder 56 would typically be between 5 and 10 mm. What is most important is that the length "L" should not be more than 10% as long as the guiding catheter 40 and ideally the length "L" is less than 1% as long as the guiding catheter 40. The shorter the length, the less will be the frictional force against the interior wall of the guiding catheter 40. The ideal material for the slit cylinder 56 is a shape memory alloy and the ideal shape memory alloy would be super elastic Nitinol.

As seen in FIGS. 4, 5 and 6, the expandable legs 54 with radiopaque feet 55 are joined to slit cylinder 56. The feet 55 (as well as other parts of the ostial stent positioner 50) could be made radiopaque by plating with a highly radiopaque metal such as platinum, gold or tantalum or they could be made from a high density metal. An important feature of the ostial stent positioner 50 is that the angle "A" of the slit cylinder 56 as shown in FIG. 6 is approximately 20 degrees and certainly less than 30 degrees. This small angle allows the ostial stent positioner 50 to be back loaded into the guiding catheter 40 without requiring a special introducer device as was described in a prior application. Furthermore, if the interventional cardiologist accidentally advances the slit cylinder 56 beyond the distal end of the guiding catheter 40, the ostial stent positioner 50 can be readily pulled back into the guiding catheter 40. Therefore, the designs shown in FIGS. 4, 5, and 6 are an improvement over prior designs because the ostial stent positioner 50 is easier to place into the guiding catheter 40 without requiring an additional introducer tool and without requiring an additional step in the method for placing a stent at the ostium of an artery.

To introduce a stent delivery system into a coronary artery, the typical diameter for the guiding catheter 40 would be 6, 7 or 8 French (Fr). It would be highly desirable for the ostial stent positioner 50 to be made with a single diameter of its slit cylinder 56 that holds the expandable legs 54. This would decrease the inventory requirements for the positioner 50 for each catheterization lab that performs coronary interventions. Specifically, only one diameter of the slit cylinder 56 would be required and it would fit into guiding catheters that are either 6, 7 or 8 Fr. It would also be highly desirable to have the cylinder 56 (as shown in FIGS. 4, 5 and 6) expand radially outward to gently press against the inner surface of the guiding catheter 40. To have a single product that would be suitable for 6, 7 or 8 Fr guiding catheters, the outer diameter of the slit cylinder 56 when free in air should be approximately the inside diameter of an 8 Fr guiding catheter. Such a cylinder 56 would then also fit snugly within either 6 Fr or 7 Fr guiding catheters. The wall thickness for the slit cylinder 56 would ideally be between 0.001 and 0.003 inches.

It should also be understood that a larger diameter guiding catheter 40 could be used specifically for treating an ostial stenosis in a renal artery. Guiding catheters as large as 14 Fr or as small as 6 Fr could be used for inserting a stent into an ostial stenosis of a renal artery. Of course, the uncompressed diameter of the slit cylinder 56 must also be at least slightly larger than the inside diameter of any such guiding catheter. Therefore, it should be understood that the dimensions for the slit cylinder 56 should be somewhat larger for renal stenoses as compared to the dimensions that are optimum for stenoses of the coronary arteries. However, the length of the slit cylinder 56 of such a ostial stent positioner for stenting a renal ostial stenosis should be less than 10% of the length of the guiding catheter.

FIG. 7 is a perspective view of an alternative embodiment of the invention, which is the ostial stent positioner 60. The positioner 60 has a helical, flat wire, cylindrical body 66 that is quite flexible because of its helical design. Legs 64 with radiopaque feet 65 are attached at the distal end of the cylinder 60 and a wire 61 is attached at the proximal end of the cylinder 60. The dimensions and materials for the ostial stent positioner 60 are comparable to the dimensions and materials of the ostial stent positioner 50.

The major advantages of the designs of the slit cylinder 56 and the helical cylinder 66 as compared to the invention of Saltiel are at least two-fold: (1) the cylinders 56 and 66 are very short compared to the length of the guiding catheter 40 so that they slide easily within the guiding catheter 40; and (2) both the slit cylinder 56 and the helical cylinder 66 are each radially expandable, variable diameter cylinders so as to gently contact the interior wall of the guiding catheter 40. The important characteristic of the variable diameter cylinder 56 or 66 is that its outside diameter becomes substantially equal to the inside diameter of the guiding catheter into which the variable diameter cylinder is inserted. Two advantages of the variable diameter cylinder are that it allows for one-size-fits-all design to decrease the inventory of the ostial stent positioners in any catheterization lab and also, by being gently expanded against the wall of the guiding catheter 40, these variable diameter cylinders 56 and 66 provide the largest interior lumen which facilitates the introduction of the stent delivery system. The Saltiel invention has a fixed diameter cylinder that extends for the entire length of the guiding catheter and therefore a different size of ostial stent positioner would be required for each different diameter of the guiding catheter. An additional disadvantage of the Saltiel invention is that the full length cylinder within the guiding catheter would be very difficult to advance or pull back because the frictional forces would be very large. In addition, there would be severe limitations for radiopaque contrast injection through the Saltiel device due to increased fluid impedance.

Figure 8:
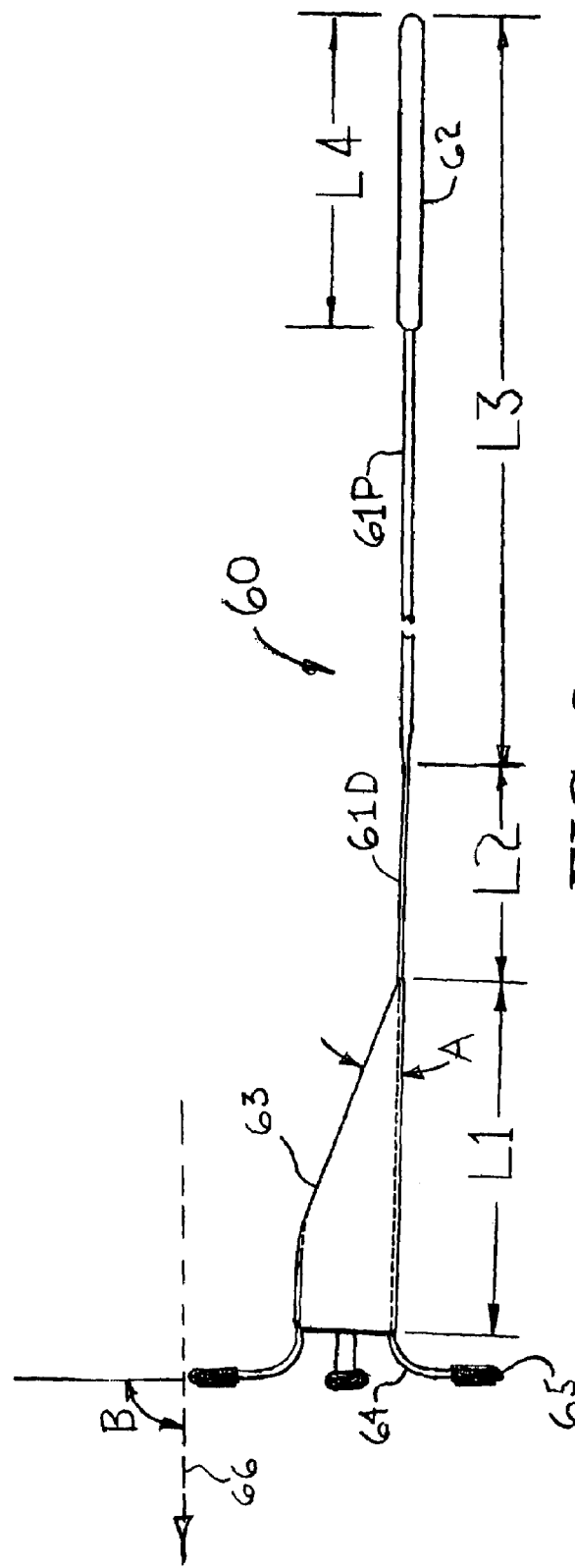
FIG. 8 is a side view of an alternative embodiment of the present invention showing legs that extend to be at an angle of approximately 90 degrees relative to the longitudinal axis of the positioner when the legs are pushed against the wall of the aorta and also showing a smaller diameter for the wire where it attaches to the slit cylinder.

Another alternative embodiment of the present invention is the ostial stent positioner 60 that is shown in FIG. 8. This positioner 60 has a short distal wire section 61D, a much longer proximal wire section 61P, a handle 62 and a short, slit, variable diameter cylinder 63 having a multiplicity of legs 64 having radiopaque feet 65. In FIG. 8, the direction of the longitudinal axis of the positioner 60 is shown as the line 66. When deployed in air, the angle "B" between the direction 66 and the long axis of the feet 65 should be between 60 and 90 degrees. This is quite different from the design of the positioner 50 where the angle "B" is approximately 45 degrees. Having an angle "B" in air of at least 60 degrees provides better contact with the wall of the aorta when the positioner 60 is pushed against that wall. The length L1 of the variable diameter cylinder 63 should be between 0.5 and 3.0 cm. As with the slit cylinder 56 of FIG. 6, the angle "A" should be about 20 degrees for easily pulling of the positioner 60 back into the distal end of a guiding catheter.

An important improvement of the design of positioner 60 is that there is a more flexible section 61D of the wire that moves the cylinder 63 back and forth in the guiding catheter. The section 61D should have a length L2 that lies between 1 and 10 cm and should have a wire diameter of between 0.01 and 0.02 inches. This more flexible section prevents inadvertent bending of the curved section of the guiding catheter when the positioner 60 extends out the guiding catheter's distal end. The stiffer wire section 61P provides improved pushability and should have a length L3 that lies between 100 and 120 cm and should have a diameter that lies between 0.015 and 0.03 inches. The handle 62 should have a length L4 of at least 3 cm and a diameter of at least 0.02 inches. The handle 62 is optimally a plastic that has a bright color such as yellow, orange or red that is different from the typical gray color of a guide wire.

All other features of the design of the positioner 60 are similar to those same features of the positioner 50 of FIGS. 4, 5 and 6.

An important aspect of the design of the ostial stent positioner is that it should be coated with a lubricity agent to ease its motion through the guiding catheter. Hydrophilic polymers and silicone are examples of lubricity agents that could be used to coat at least part of the ostial stent positioner.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. An introducer sheath type of ostial stent positioner for facilitating the placement by an operator of the proximal end of a stent within ±2 mm of the ostial plane of an artery that has an ostial stenosis, the positioner having a wire extending for most of its length that is attached to a variable diameter cylinder that has an adjustable outer diameter that becomes essentially the same dimension as the inside diameter of a guiding catheter into which the variable diameter cylinder is placed, the variable diameter cylinder being designed to exert a gentle outward force against the interior wall of the guiding catheter, the wire extending for most of the length of the positioner having a distal section and a proximal section with the distal section being shorter in length and smaller in diameter as compared to the proximal section of the wire, the variable diameter cylinder also being fixedly attached to at least two expandable distal legs that end with radiopaque feet that have a substantially flat surface where they touch the surface of the aorta at the ostium of the artery to be stented, the substantially flat surfaces of the feet collectively forming a distal plane when they are pushed in a distal direction out of the distal end of the guiding catheter and against the interior wall of the aorta, the positioner being designed for placement of the distal plane of the radiopaque feet to be substantially co-planar with the ostial plane of the artery when the ostial stent positioner is urged forward in a distal direction after the expandable distal legs have been expanded radially outward beyond the distal end of the guiding catheter through which the positioner can be placed.

2. The positioner of claim 1 where the variable diameter cylinder is adapted to be placed into guiding catheters having diameters that lie between 4 F and 14 Fr.

3. The positioner of claim 1 where the wire has a handle at its proximal end to facilitate the handling of the positioner by the operator.

4. The positioner of claim 3 where the handle is formed from a plastic material having a color that is distinctly different from the gray color of a guide wire.

5. The positioner of claim 1 where the expandable legs have feet that are formed from a radiopaque metal or coated with a radiopaque metal.

6. The positioner of claim 5 where the feet on the expandable legs have an outside diameter when expanded that lies between 4 and 15 mm.

7. The positioner of claim 1 where the positioner has expandable legs that are formed from a combination of a plastic material and a metal, the combination being generally radiopaque.

8. The positioner of claim 1 where the variable diameter cylinder has expandable legs that are generally in the shape of a flower that has at least two petals.

9. The positioner of claim 8 where the cylinder's expandable legs form at least four petals.

10. The positioner of claim 1 where the variable diameter cylinder of the ostial stent positioner has a wedge-like surface for easy placement into the distal end of a guiding catheter, the wedge-like structure having an angle "A" that lies between 10 and 30 degrees.

11. The positioner of claim 1 where the variable diameter cylinder of the ostial stent positioner has a slit in its outer circumferential surface so as to have an outside diameter that is variable depending on the inside diameter of the guiding catheter into which the cylinder is inserted.

12. The positioner of claim 11 where the slit cylinder that is attached to the expandable legs has an angle where the slit cylinder is joined to the distal wire section that is less than 30 degrees.

13. The positioner of claim 1 where the variable diameter cylinder of the ostial stent positioner has a helical, flat wire, cylindrical structure so as to have an outside diameter that is variable depending on the inside diameter of the guiding catheter into which the cylinder is inserted.

14. The positioner of claim 1 where both the distal and proximal sections of the wire extending for most of the length of the positioner are formed from the metal Nitinol.

15. The positioner of claim 1 where the variable diameter cylinder is formed from a shape memory alloy.

16. The positioner of claim 15 where the shape memory alloy that is used to form the variable diameter cylinder is super elastic Nitinol.

17. An introducer sheath type of ostial stent positioner for facilitating the placement by an operator of the proximal end of a stent within ±2 mm of the ostial plane of an artery that has an ostial stenosis, the positioner having a wire extending for most of its length that is attached to a variable diameter cylinder that is adapted to be placed within a guiding catheter, the outside diameter of the variable diameter cylinder is adjustable to become substantially the same dimension as the inside diameter of the guiding catheter into which the variable diameter cylinder is inserted, the variable diameter cylinder being adapted to exert an outward gentle force, the length of the variable diameter cylinder being less than 10% of the length of the guiding catheter, the variable diameter cylinder also being attached to at least two expandable distal legs that end with radiopaque feet that have an essentially flat surface where they touch the aorta at the plane of the ostium of the artery that is to be stented, the essentially flat surfaces of the feet forming a distal plane when they are pushed in a distal direction out of the distal end of the guiding catheter and against the interior wall of the aorta, the positioner being designed for placement of the distal plane of the radiopaque feet to be substantially co-planar with the ostial plane of the artery when the ostial stent positioner is urged forward in a distal direction after the expandable distal legs have been expanded radially outward beyond the distal end of the guiding catheter.

18. The positioner of claim 17 where the variable diameter cylinder is a slit cylinder.

* * * * *